United States Patent [19]

Tam

[11] Patent Number: 5,390,112
[45] Date of Patent: Feb. 14, 1995

[54] THREE-DIMENSIONAL COMPUTERIZED TOMOGRAPHY SCANNING METHOD AND SYSTEM FOR IMAGING LARGE OBJECTS WITH SMALLER AREA DETECTORS

[75] Inventor: Kwok C. Tam, Schenectady, N.Y.

[73] Assignee: General Electric Company, Schenectady, N.Y.

[21] Appl. No.: 131,180

[22] Filed: Oct. 4, 1993

[51] Int. Cl.⁶ .............................................. G06F 15/42
[52] U.S. Cl. ................................................ 364/413.15
[58] Field of Search ...................... 364/413.15, 413.14, 364/413.22, 413.16; 378/4, 20, 12

[56] References Cited

U.S. PATENT DOCUMENTS

| | | | |
|---|---|---|---|
| 4,789,929 | 12/1988 | Nishimura et al. | 364/413.15 |
| 5,032,990 | 7/1991 | Eberhard et al. | 364/413.15 |
| 5,073,911 | 12/1991 | Ozaki et al. | 364/413.15 |
| 5,187,659 | 2/1993 | Eberhard et al. | 364/413.15 |
| 5,208,746 | 5/1993 | King et al. | 364/413.15 |
| 5,291,402 | 3/1994 | Pfoh | 364/413.15 |
| 5,325,296 | 6/1994 | Eberhard | 364/413.15 |

OTHER PUBLICATIONS

"Cone-beam Tomography: Recent Advances and a Tutorial Review", Bruce D. Smith, Optical Engineering-May 1990, vo. 29, No. 5-pp. 524-534.

"Image Reconstruction from Cone-Beam Projections: Necessary and Sufficient Conditions and Reconstruction Methods", Bruce D. Smith, IEEE Tranactions on Medical Imaging, vol. MI-4, No. 1, Mar. 1985, pp. 14-25.

"Three-Dimensional Helical-Scan Computed Tomography Using Cone-Beam Projections", Hiroyuki Kudo and Tsuneo Saito, Systems and Computers in Japan, vol. 23, No. 12, 1992, pp. 75-82.

*Primary Examiner*—Donald E. McElheny, Jr.
*Attorney, Agent, or Firm*—Enrique J. Mora; Paul R. Webb, II

[57] ABSTRACT

Complete cone beam scanning and data acquisition techniques are provided for three-dimensional computerized tomography imaging of an object. Such techniques include defining a source scanning trajectory such as a helical path located on a cylindrical surface which surrounds a field of view that contains the object. The foregoing scanning trajectory allows using area detectors having a predetermined dimension (such as height or width) substantially smaller than the corresponding dimension of the object to be imaged.

30 Claims, 5 Drawing Sheets

THREE-DIMENSIONAL COMPUTERIZED TOMOGRAPHY SCANNING METHOD AND SYSTEM FOR IMAGING LARGE OBJECTS WITH SMALLER AREA DETECTORS

BACKGROUND OF THE INVENTION

The present invention relates generally to three-dimensional (3D) computerized tomography (CT) and, more particularly, the present invention relates to a scanning method and system for imaging relatively large objects with relatively small area detectors.

In conventional computerized tomography for both medical and industrial applications, an x-ray fan beam and a linear array detector are used. Two-dimensional (2D) imaging is achieved. While an acquired data set may be complete and image quality is correspondingly high, only a single slice of an object is imaged at a time. When a 3D image is required, a stack of slices approach is employed. Acquiring a 3D data set one 2D slice at a time is inherently slow. Moreover, in medical applications, motion artifacts occur because adjacent slices are not imaged simultaneously. Also, dose utilization is less than optimal because the distance between slices is typically less than the x-ray collimator aperture, resulting in double exposure to many parts of the body. In 2D CT, the scanning path of the source is often a simple circular scan about the object. The linear array detector is fixed relative to the source. (Although it is usual to talk about a scan path of a source relative to the object to be imaged, it is to be appreciated that the object may be rotated or otherwise moved to provide relative motion between the object and the source.)

In a system employing true cone beam geometry for 3D imaging, a cone beam x-ray source and a 2D area detector are used. An object is scanned, preferably over a 360° angular range either by moving the x-ray source in a scanning circle or other path about the object or by rotating the object while the source remains stationary. In either case, the area detector is fixed relative to the source. The relative movement between the source and object which is to be imaged provides scanning in either case. Compared to the conventional 2D stack of slices approach to achieve 3D imaging, the cone beam geometry has the potential to achieve rapid 3D imaging of both medical and industrial objects with improved dose utilization.

The 2D area detector used for 3D imaging generally has detector elements arranged in rows and columns. Such area detectors, using an array of detector elements, have had either flat or curved geometry. In other words, the rows and columns have been arranged in a plane for flat geometry detectors and have been arranged in curves for curved geometry detectors. Available area detectors have generally been of large size and low quality, such as x-ray image intensifiers, or of small size and higher quality. High costs and other factors have made high quality, high resolution, large area 2D array detectors generally unavailable.

U.S. Pat. No. 5,032, 990, issued Jul. 16, 1991, entitled "TRANSLATE ROTATE SCANNING METHOD FOR X-RAY IMAGING," assigned on its face to the assignee of the present application, and hereby incorporated by reference, discloses a technique for two-dimensional imaging of an object which is so wide that a linear array detector is not wide enough to span the object or part which is to be viewed.

U.S. Pat. No. 5,187,659, issued Feb. 16, 1993, entitled "CONE BEAM SCANNING TRAJECTORIES FOR THREE-DIMENSIONAL COMPUTERIZED TOMOGRAPHY DATA ACQUISITION WHERE OBJECT IS LARGER THAN THE FIELD OF VIEW," assigned to the assignee of the present application, and hereby incorporated by reference discloses a technique for avoiding corrupted data when performing 3D CT on an object larger than the field of view.

U.S. patent application Ser. No. 07/998,330, filed Dec. 30, 1992, U.S. Pat. No. 5,319,693, in the name of Eberhard et al., entitled "THREE-DIMENSIONAL COMPUTERIZED TOMOGRAPHY SCANNING CONFIGURATION FOR IMAGING LARGE OBJECTS WITH SMALLER AREA DETECTORS", assigned to the assignee of the present application, and hereby incorporated by reference, discloses a technique for three-dimensionally imaging relatively large objects using relatively small area detectors by changing the configurations corresponding to the relative positioning of a source of cone beam energy, the object which is to be imaged, and the area detector.

Kudo and Saito (hereinafter Kudo) disclose a helical scanning technique in an article entitled "Three-Dimensional Helical Scan Computed Tomography Using Cone-beam Projections", Journal of Systems and Computers in Japan, Vol. 23, No. 12, pp. 75–82 (1992) and hereby incorporated by reference. However, Kudo fails to disclose in the above article how such technique can be effectively used for exactly reconstructing the image of the object under inspection being that Kudo's technique at best only provides an approximate reconstruction technique. Further, although Kudo discloses a helical scanning technique which can be utilized to reduce a predetermined dimension (such as height or width) of the area detector such reduction is limited to at least twice the helix pitch spacing between consecutive stages formed by a given helical scan path assuming a constant helix pitch spacing. Thus, Kudos's scanning technique does not suggest how to reduce such predetermined dimension by two to one so as to span just the spacing between any two consecutive stages of the helical scanning path, again assuming a constant helix pitch spacing. (No representation is made or intended that this referenced article or previously referenced application or issued patents are necessarily prior art to the present application.)

OBJECTS AND SUMMARY OF THE INVENTION

Accordingly, it is a general object of the present invention to provide an improved 3D CT imaging technique.

A more specific object of the present invention is to provide for imaging of relatively large objects without requiring large detectors.

Yet another object of the present invention is to provide a technique which allows for using the same small detector for imaging objects of vastly varying dimensions such as height or width.

It is yet another object of the present invention to provide a technique for realizing reduced costs through the use of a small detector and associated detector electronics.

The foregoing and other objects and advantages of the present invention which will become more apparent from the following detailed description are realized by a scanning and data acquisition method for three dimensional computerized tomography (CT) imaging of an object in a field of view radially centered on a predetermined axis. Cone beam energy is applied from a cone beam source to at least a portion of the object. A source scanning trajectory is defined as a path traversed by the source. The cone beam source is used fixed relative to an area detector with both source and detector movably positioned relative to the object to scan about the object. Such use of the cone beam source includes moving the object relative to the source or moving the source relative to the object. In either case the source scanning trajectory is specified as a helical path defining a plurality of mutually spaced stages on a predetermined geometric surface surrounding the field of view such that each plane passing through the field of view intersects the scanning trajectory in at least one point. The predetermined geometric surface which surrounds the field of view as well as the field of view can each be conveniently represented by respective cylindrical surfaces. In accordance with one embodiment of the present invention, the area detector has a predetermined dimension (such as height or width) extending sufficiently along a direction generally parallel to the predetermined axis to span at least the two consecutive stages having the largest spacing therebetween, thereby obviating the predetermined dimension of the detector from fully spanning the field of view along the predetermined axis. Scanning is performed at a plurality of positions along the source scanning trajectory to acquire cone beam projection data corresponding to respective portions of the object. The acquired cone beam projection data can be used to provide a complete data set which can be exactly reconstructed into an image of the object which may be displayed or stored for subsequent analysis.

The three-dimensional computerized tomography system according to the present invention includes a cone beam energy source for applying cone beam energy to at least a portion of the object to be imaged. A two-dimensional detector is positioned to receive cone beam energy from the source. A scanning device causes relative motion of file source and the object such that the source moves along a scanning trajectory relative to the object. A trajectory defining means is operatively coupled to the scanning device to provide a helical path as previously described. Means for acquiring cone beam projection data with the source at a plurality of positions along the source scanning trajectory is used in order to acquire cone beam projection data corresponding to respective portions of the object. Means for using the acquired cone beam projection data (such as a computer workstation or the like) is utilized to generate a complete data set which can be exactly reconstructed into an image of the object. A display can be connected to the computer workstation for displaying a CT image of the entire object based upon the generated data set.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description in conjunction with the accompanying drawings in which like characters represent like parts throughout the drawings, and in which:

DETAILED DESCRIPTION OF THE INVENTION

Figure 1A:
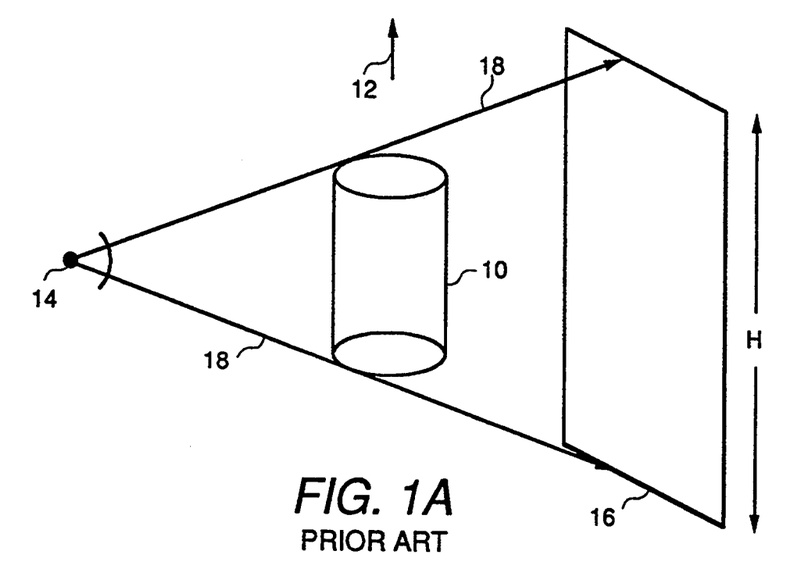
FIG. 1A depicts one typical prior art configuration wherein a cone beam energy source and a two-dimensional area detector scan an exemplary field of view which may contain a subsection of an object to be imaged and wherein the height of the detector, for example, must be sufficiently large in order to fully span the exemplary field of view.

A typical scanning and data acquisition configuration employing cone beam geometry is depicted in FIG. 1A. A field of view 10 such as a cylinder which can be radially centered on a predetermined axis 12 encloses an object to be imaged (not shown) or a subsection of a workpiece which exceeds the size of the field of view. More generally, it will be understood that the object is not necessarily a workpiece or a portion thereof, but may be a human or animal patient or portion thereof which is to be imaged for medical purposes. In either case, a suitable cone beam energy source 14 and a typical two dimensional array detector 16 cooperate along a defined source scanning trajectory (not shown in FIG. 1A) in a manner generally well understood by those skilled in the an to provide cone beam projection data. Whether the object is pan of a workpiece being analyzed for industrial purposes, or a portion of a human or a animal patient being analyzed for medical purposes, the frame of reference which will be generally used in this discussion will be the frame of reference of the object in field of view 10. Thus, the discussion will refer to the trajectory or scan path of source 14. However, it will be understood that the relative motion between source 14 and the object may be accomplished by: moving source 14 while the object in field of view 10 remains stationary, moving the object while source 14 is stationary, or by moving both the object and source 14 at the same time. In medical applications where the object is a patient or part of a patient, source 14 is usually moved while the patient is stationary. In industrial applications where the object may be part or all of a workpiece, the workpiece is usually moved while the source 14 is maintained stationary.

As is generally appreciated in the field of three-dimensional computerized tomography (CT), area detector 16 detects cone beam energy which has passed through at least a portion of the object to be imaged.

Usually, and as contemplated by the present invention, the area detector would be fixed relative to source 14, that is, the detector would move relative to the object, but not relative to the source 14. However, the present invention does not necessarily require that the area detector is fixed relative to source 14.

The source 14 is preferably an x-ray cone beam energy source, but could be alternatively a source of neutrons, positrons, or other form of radiation or electromagnetic energy from a point source.

It should be appreciated that as shown in FIG. 1A, area detector 16 generally has a predetermined dimension such as height dimension H which must extend sufficiently along the predetermined axis 12 so as to fully span the field of view along axis 12. For example, in FIG. 1A, such height dimension must extend sufficiently in order to detect exemplary rays 18 which as seen in FIG. 1A fully span the field of view along axis 12. In other words, the prior art configuration illustrated in FIG. 1A typically requires the use of an area detector tall enough to span the entire height of the field of view which contains the object in order to capture the entire cone beam projection data of the object, i.e., complete cone beam data for allowing computation of Radon data in an exact manner.

Figure 1B:
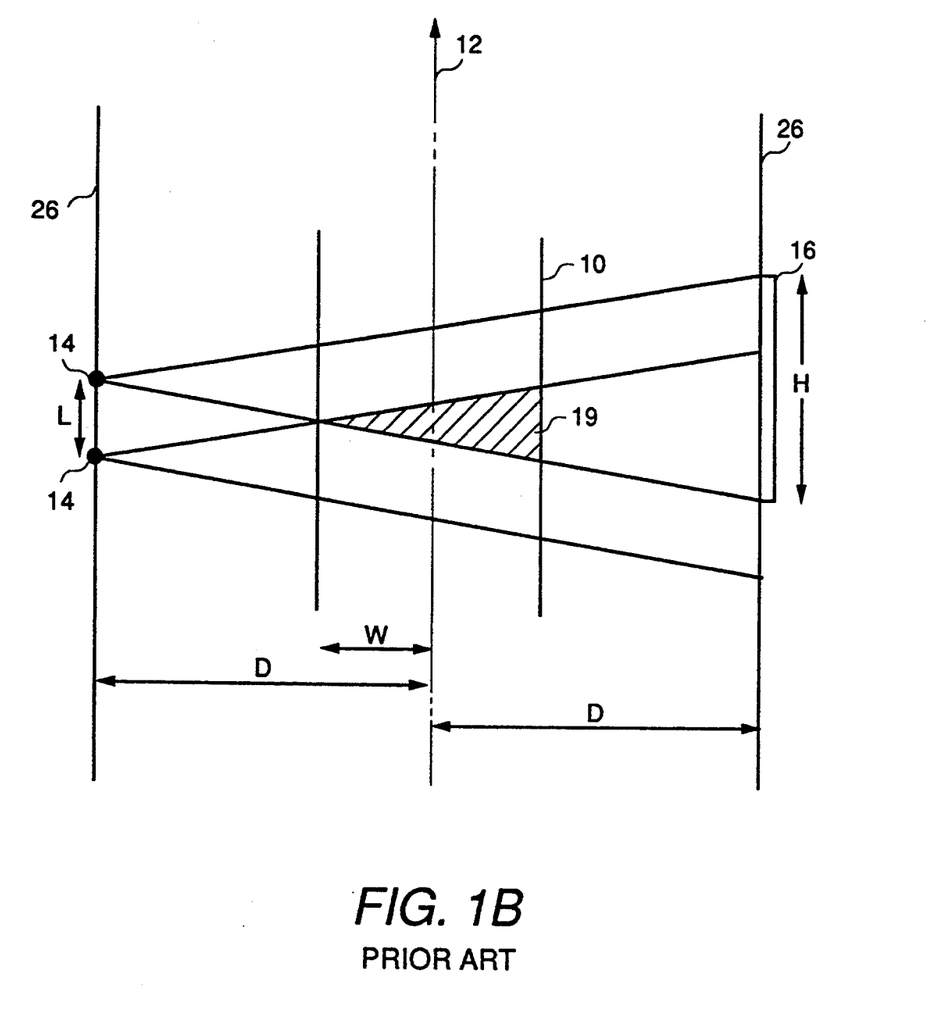
FIG. 1B depicts another typical prior art configuration analogous in operation to FIG. 1A except that the height of the detector is not required to fully span the exemplary field of view.

FIG. 1B depicts the prior art configuration disclosed by the Kudo article previously cited in the background of the invention section of the present disclosure. This prior art configuration although not requiting the height of the detector, for example, to fully span the exemplary field of view, such configuration imposes dimensional constraints which are overcome by the present invention. Similar to FIG. 1A, the field of view 10 such as a cylinder encloses the object to be imaged (not shown). The cone beam energy source 14 and the area detector 16 cooperate along a helical scanning trajectory (not shown in FIG. 1B) situated along the surface of a cylinder 26. For the exemplary geometric representation illustrated in FIG. 1B, the Kudo article can be shown to disclose that for a given helix pitch spacing represented by L such spacing limits the height H of detector 16 as follows:

$$H = L \times \frac{2D}{D - w} \quad \text{(Eq. 1)}$$

where D is the radius of cylinder 26 and w is the radius of the cylindrical field of view 10. Through simple mathematical derivation it can be further shown that Equation 1 must satisfy a dimensional constraint such that $H > L \times 2$ which simply means that the height of detector 16 has to be larger than twice the helix pitch spacing L. As seen in FIG. 1B, the helix pitch spacing L refers to the spacing between consecutive stages (such as the turns or revolutions) traversed by the cone beam source along the helical scanning path. As will be described in further detail shortly hereafter the method of the present invention is not limited to the foregoing dimensional constraint being that the present invention sole dimensional constraint is that a predetermined dimension of the detector, such as height for example, extends sufficiently to span just the distance L (not $L \times 2$) between any two consecutive stages, assuming a helical scanning path having a constant or equidistant helix pitch spacing. In the general case of a helical scanning path having a variable helix pitch spacing then the present invention advantageously provides that the height of the detector extends just sufficiently to span at least the two consecutive stages having the largest spacing therebetween. In other words in accordance with the present invention so long as H=L complete data can be acquired to exactly image the object within the field of view 10. This represents a distinctive advantage over Kudo being that for a helical scanning path having a predefined helix pitch spacing the present invention allows at least a two to one reduction of such predetermined dimension of the detector which in turn allows for a more economical scanning technique. As shown in FIG. 1B, the Kudo technique further requires that cone beam energy must penetrate through an overlying portion 19 represented by the cross hatched portion in the field of view 10. A reconstructed image therefore contains contributions from this overlying portion and image corruption is likely by data resulting from the overlying portion. Further, in medical applications the Kudo technique is less than optimal because the overlying portion results in double x-ray exposure to many parts of the body.

Figure 2:
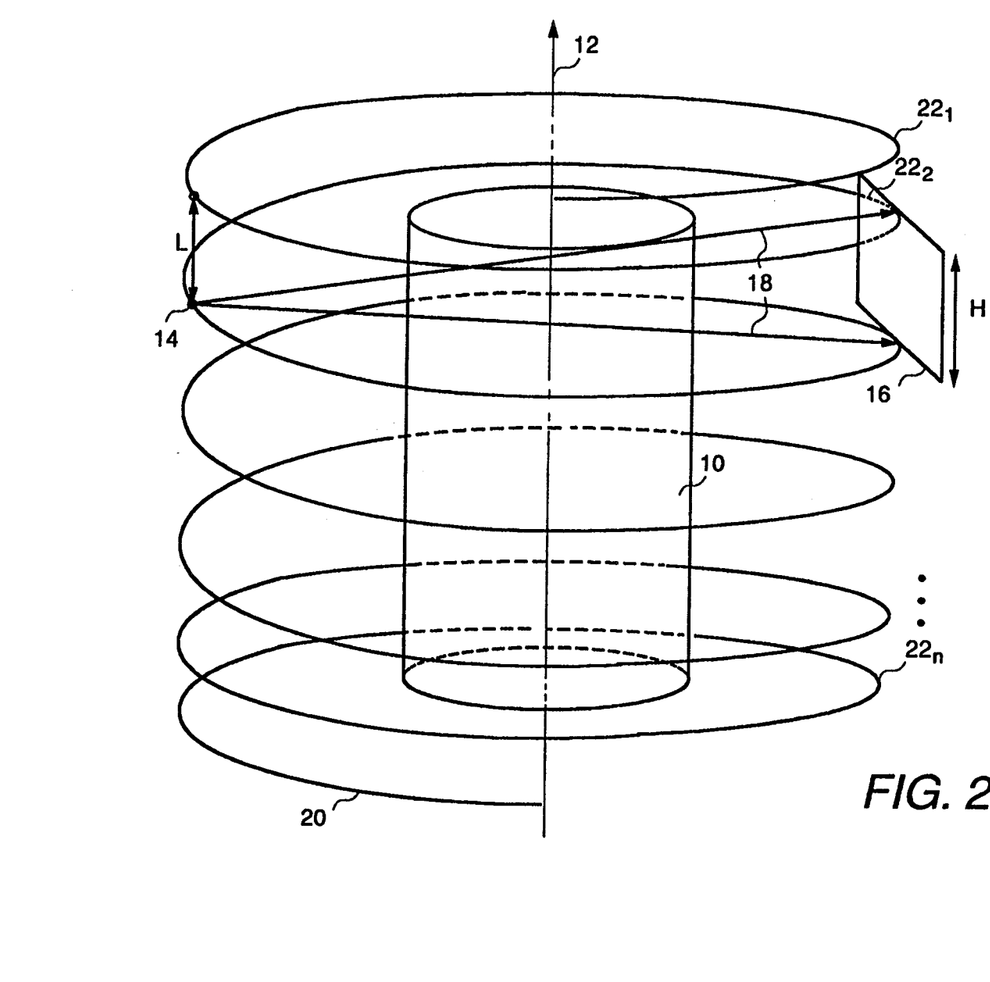
FIG. 2 depicts an embodiment of the present invention wherein a source scanning trajectory is a helical path having a plurality of stages for scanning a field of view having a substantially larger height dimension than the area detector, for example.

Turning now to FIG. 2, a scanning trajectory 20 in accordance with the present invention is shown. Specifically, the source scanning trajectory 20 is a helical path located on the surface of a predetermined geometric surface (not shown in FIG. 2) such as a cylinder radially centered on axis 12. It is understood that such geometric surface need not be an actual physical surface. Helical path 20 defines a plurality of stages $21_1, 22_2, \ldots 22_n$ mutually spaced and surrounding the field of view 10 such that each plane passing through the field of view intersects the scanning trajectory in at least one point. As used herein the term stage refers to each of the turns or revolutions formed by the helical path about axis 12 for example. As shown, by Bruce D. Smith in an article entitled "Image Reconstruction from Cone-Beam projections: Necessary and Sufficient Conditions and Reconstruction Methods," IEEE Transactions on. Medical. Imaging, Vol. MI-4, No. 1, pp. 14–25, (March 1985), the foregoing criterion ensures that the cone beam data set acquired via such scanning trajectory is complete. In other words, the acquired cone beam data set is complete if each plane passing through the object cuts the scanning trajectory in at least one point. This criterion generally assumes that the detector is fixed relative to the source and that the entire object can be scanned within the field of view of the source. As explained in the context of FIG. 1A, for example, the height of the area detector imposes a limit on the height of the object which can be entirely spanned by a given area detector being that taller objects would require correspondingly taller detectors. As further explained in the context of FIG. 1B, the helix pitch spacing imposes a limit of the height of the detector, namely $H > L \times 2$. However, as shown in FIG. 2 and in accordance with a key advantage of the present invention, the foregoing criterion can be advantageously satisfied if the height dimension of the detector extends just sufficiently along a direction generally parallel to axis 12 to span at least the two consecutive stages in the helical path having the largest spacing therebetween as represented by L, that is, the largest spacing between corresponding points of such consecutive stages along axis 12. Thus, it will be appreciated that the spacing between successive stages could vary depending on the specific scanning implementation. Alternatively, the scanning trajectory may be comprised of stages wherein the spacing between any two successive stages along axis 12 is substantially equidistant.

It should be understood, that axis 12 as depicted in FIGS. 1A, 1B, 2 and 3 is shown as extending in a vertical direction, however, axis 12 could alternatively extend along a horizontal direction and in such case the predetermined dimension of the detector which would be applicable would correspond to the width dimension of the area detector. Thus, depending on the particular geometric arrangement of a given implementation, the predetermined dimension of the area detector (such as either the height or width dimension of the area detector) could be advantageously reduced relative to the corresponding dimension of the object to be imaged. The foregoing key advantage provided by the present invention thereby obviates the predetermined dimension of the detector from fully spanning the field of view along axis 12, for example. Further such key advantage provided by the present invention allows for two to one reduction of the predetermined dimension for a given helix pitch spacing. As shown in FIG. 2, cone beam CT scanning is achieved with a detector being substantially shorter than the height dimension of the field of view.

Figure 3:
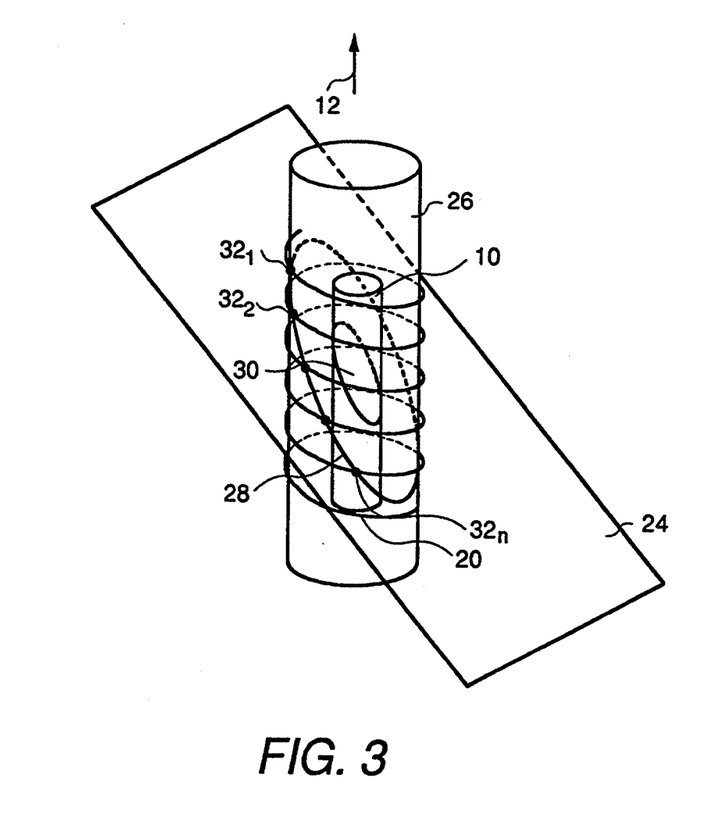
FIG. 3 depicts an isometric view of an exemplary planar intersection through the surface of a cylinder defined by the helical scanning trajectory, wherein such defined cylinder encloses the field of view in accordance with the present invention.

As shown in FIG. 3, any plane 24 intersecting the field of view 10 must also intersect the boundary of the geometric surface which surrounds the field of view being that the scanning trajectory 20 is defined upon such geometric surface. In the case illustrated in FIG. 3, the geometric surface clearly corresponds to the surface of a cylinder 26 which surrounds the field of view 10. The curve of intersection between plane 24 and cylinder 26 thus is an ellipse identified by numeral 28 and referred herein as scanning ellipse. Inspection of FIG. 3 further shows that the curve of intersection between plane 24 and the cylindrical field of view 10 is also an ellipse which is enclosed by scanning ellipse 28 and being identified by numeral 30. Therefore, it should be appreciated that since the scanning helical path lies on the surface of cylinder 26, then the scan path intersects plane 24 at points $32_1 \ldots 32_n$ that collectively lie on the boundary of the geometric surface upon which the helical path is defined, that is, such points of intersection lie on scanning ellipse 28.

In order to image the object within the field of view 10, Radon data for the portion of the plane 24 that lies within the field of view is used. Techniques for allowing computation of Radon data from cone beam projection data can be performed in known fashion and need not be described in detail. Briefly, most image reconstruction procedures in x-ray CT are based on the Radon inversion process, in which the image of an object is reconstructed from the totality of the Radon transform of the object. The Radon transform of a 3D object consists of planar integrals. The cone beam projection data, however, is not directly compatible with image reconstruction through inverse Radon transformation, which requires the use of planar integrals of the object as input. Consequently, image reconstruction by inversion from cone beam scanning data generally comprises two steps. A first step is to convert the cone beam data to planar integrals. A second step is then to perform an inverse Radon transform on the planar integrals to obtain the image.

The first step is described by the present inventor's allowed application Ser. No. 07/631,815, filed Dec. 21, 1990, U.S. Pat. No. 5,257,183, entitled "METHOD AND APPARATUS FOR CONVERTING CONE BEAM X-RAY PROJECTION DATA TO PLANAR INTEGRALS AND RECONSTRUCTING A THREE-DIMENSIONAL COMPUTERIZED TOMOGRAPH (CT) IMAGE OF AN OBJECT", assigned to the assignee of the present application and hereby incorporated by reference. A technique for performing an inverse Radon transform on planar integrals to obtain an image is described in the present inventor's prior U.S. patent application Ser. No. 07/631,818, filed Dec. 21, 1990, now abandoned entitled "PARALLEL PROCESSING METHOD AND APPARATUS FOR RECONSTRUCTING A THREE-DIMENSIONAL COMPUTERIZED TOMOGRAPHY (CT) IMAGE OF AN OBJECT FROM CONE BEAM PROJECTION DATA OR FROM PLANAR INTEGRALS", assigned to the assignee of the present application, and hereby incorporated by reference. Thus, those two prior incorporated by reference U.S. patent applications describe techniques which may be used for three-dimensional image reconstruction by Radon inversion from cone beam projection data.

Figure 4:
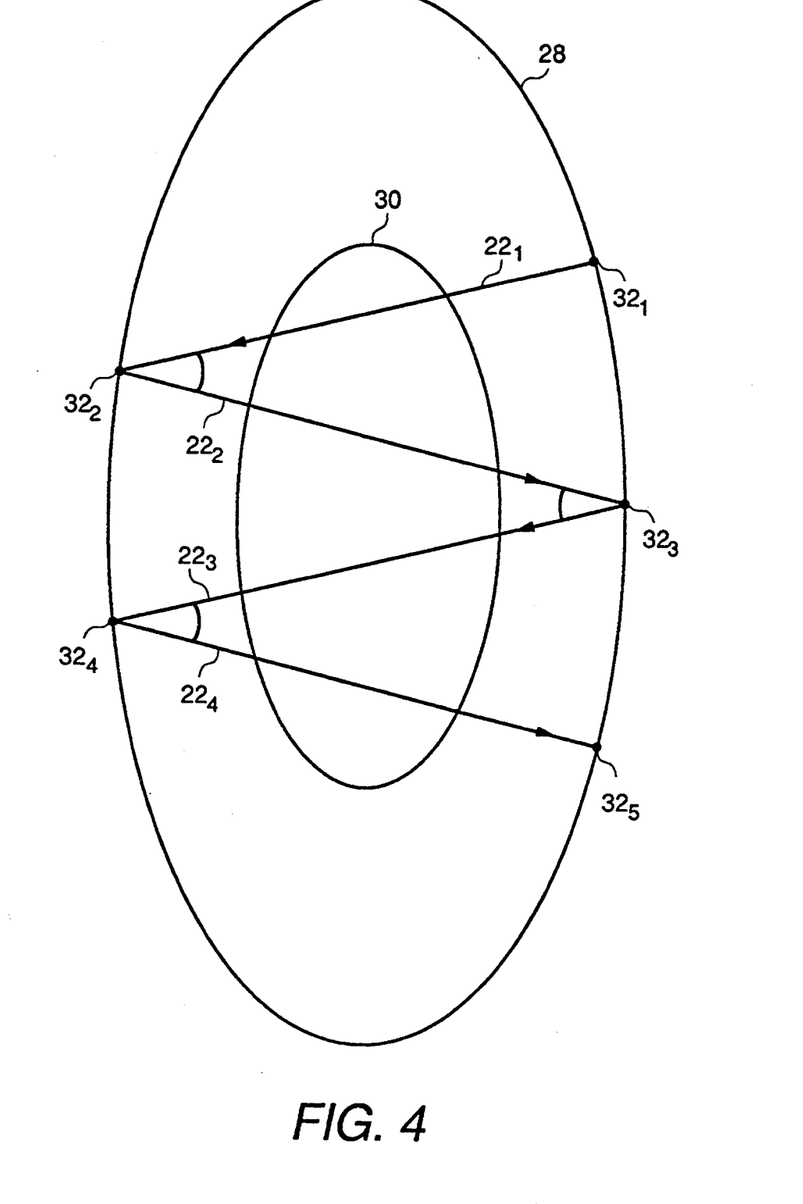
FIG. 4 illustrates a sectional view of the planar intersection shown in FIG. 3 wherein scanning at a plurality of positions on the source scanning trajectory allows to obtain cone beam projection data corresponding to respective portions of the object to be imaged.

As conceptually illustrated in FIG. 4, the foregoing Radon data can be obtained by using the cone beam projection data obtained by scanning at a plurality of positions which correspond to points of intersection along the source scanning trajectory. FIG. 4 illustrates an exemplary case wherein five scan positions corresponding to five points of intersection are used to generate a complete data set which can be exactly reconstructed into a three-dimensional image of the object. In FIG. 4 the region bounded within ellipse 30 corresponds to the portion of plane 24 which intersects field of view 10. For example, at scan position corresponding to point $32_1$ cone beam data is acquired for the portion of plane 24 located above stage $22_1$. At scan position corresponding to point $32_2$ cone beam data is similarly acquired for the portion of plane 24 bound by stages $22_1$ and $22_2$. At scan position corresponding to point $32_3$ cone beam data is acquired for the portion of plane 24 bound by stages $22_2$ and $22_3$. At scan position corresponding to point $32_4$ cone beam data is acquired for the portion of plane 24 bound by stages $22_3$ and $22_4$. Finally at scan position corresponding to point $32_5$ cone beam data is acquired for the portion of plane 24 below stage $22_4$. Since the five partial planes in the foregoing five scan positions do not overlap (i.e., they do not form an overlying portion within the field of view 10) and collectively they completely cover the portion of plane 24 that intersects the field of view in which the object to be imaged is situated, then such acquired cone beam data can be used to obtain a complete data set which can be exactly reconstructed into an image of the object without introducing data corruption.

Figure 5:
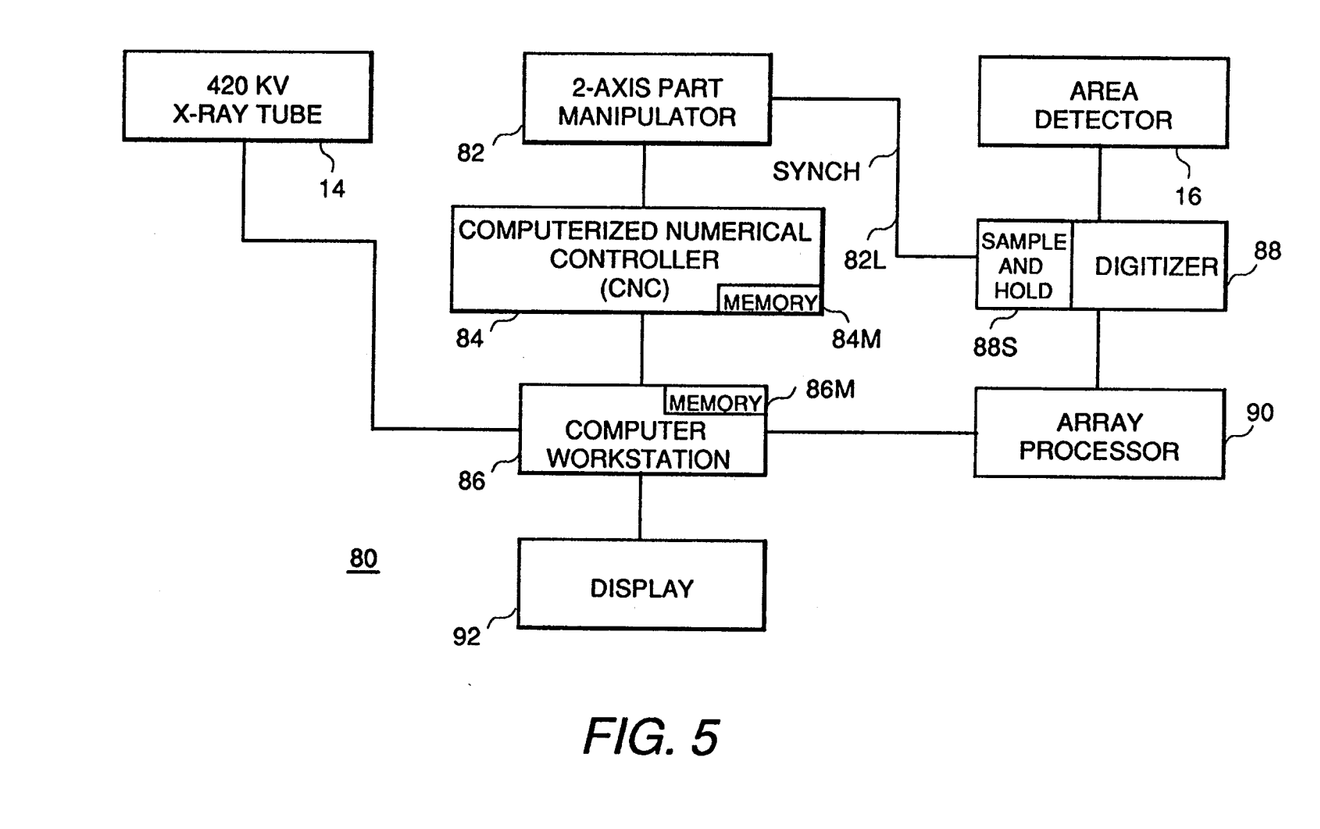
FIG. 5 is a simplified block diagram illustrating the components of the system of the present invention.

Turning now to FIG. 5, a system 80 according to the present invention will be discussed. The system includes the cone beam energy source 14 and area detector 16. Although the source 14 is shown as an x-ray tube, the cone beam energy source 14 could alternatively provide neutrons, positrons, or other forms of radiation or electromagnetic energy from a point source. Alternatively, other forms of imaging energy might be used.

A manipulator 82, which may be a two-axis part manipulator, is an example of a scanning device used to provide the relative scanning movement between the object (not shown in FIG. 5) which is to be imaged and the source 14. Although the manipulator 82 is designed to move the object, the manipulator 82 might alternatively move the source 14.

The manipulator 82 is controlled by a known computerized numerical controller (CNC) 84, which may, for example, be of a type made by Aerotech. The controller 84 may include a memory 84M having suitable data defining the helical scan path in known fashion. Alternatively, and also using well known techniques, a memory 86M of a computer work station 86, which is connected to the controller 84, may have the data which defines movements of the manipulator 82 and therefore defines the helical scan path or trajectory of the type previously discussed with respect to FIGS. 2, 3 and 4 of the present application. The computer work station 86 may be a work station made by Sun, although other computer work stations and possibly even personal computers might be used in place of the work station. The computer work station controls the other components of the system 80 in known fashion.

Connected to the area detector 16 is a digitizer 88 which operates in known fashion to convert analog signals from the area detector into digital signals representative of the image of the object under test. The digitizer 88 may include sample and hold circuits 88S operating in response to a synch signal on line 82L in known fashion. Thus, digitizer 88 provides suitable means for acquiring cone beam projection data with the source at a plurality of positions along the source scanning trajectory as described in the context of FIG. 4.

The digitized values corresponding to the detected cone beam energy, i.e., cone beam projection data from the detector elements within detector 16, are supplied from the digitizer 88 to a data array processor 90. The array processor 90, which may be of a known commercially available type such as a Meiko M40, provides the necessary signal processing for the signals coming from the digitizer 88. The array processor 90 may perform the necessary image reconstruction and processing such that a display might be connected directly to the array processor to display the images from the CT scan. However, in the arrangement shown in FIG. 5, the image data from array processor 90 is supplied to computer work station 86 and the computer work station 86 in turn supplies the data, with or without further processing, to a display 92 which displays the CT images. The computer 86 or, more preferably, array processor 90 reconstructs an image from a generated data set resulting from combining cone beam data corresponding to respective portions of the object. Thus, either computer workstation 86 or array processor 90 provide suitable means for using the acquired cone beam data to generate the complete data set which can be exactly reconstructed into an image of the object.

Upon suitable operation of the manipulator 82, the system 80 of FIG. 5 may be used to realize techniques described in the context of FIGS. 2, 3, and 4. That is, the manipulator 82 may simply move the object (not shown in FIG. 5) in a scanning movement relative to source 14 along scanning trajectory 20. It will be appreciated that the scanning movement along the scanning trajectory can be either step-wise or continuous scan depending on the particular implementation.

Stored within memory 84M or memory 86M would be a program having a module which controls manipulator 82 and/or possibly a second manipulator (not shown) in order to position the object, source, and area detector in suitable scanning positions. Another module of the program, most likely stored in memory 86M, would acquire the cone beam data corresponding to each of the respective portions of the object. The program would further include a module for using the cone beam data to provide the data set corresponding to the whole object. The cone beam data corresponding to respective portions of the object can be used to generate such complete data set corresponding to the whole object by simply combining the cone beam data in the manner discussed with respect to FIG. 4.

Although various specific constructions have been given for the present invention, it is to be understood that these are for illustrative purposes only. Various modifications and adaptations will be readily apparent to those of skill in the art. For example, although the present invention has been described with reference to a source which physically moves relative to the object during the scanning operation, an alternative is possible. In such an alternative, a material may be around or partially around the object to be viewed, which material generates imaging energy upon being struck by a different kind of energy beam. The beam applied to the source material causes the source material to in turn emit an imaging energy. Although the source is not physically moved relative to the object, the source would effectively be scanned or moved relative to the object by sweeping the beam striking the source material in a helical path corresponding to the trajectory. In similar fashion and as used herein, scanning or moving the source relative to the object shall include situations where a series of sources are turned on sequentially to effectively scan or move the source as well as the beam striking a source material type of source movement. In view of these and other modifications, the scope of the present invention should be determined by reference to the claims appended hereto.

What is claimed:

1. A scanning and data acquisition method for three dimensional computerized tomography (CT) imaging of an object in a field of view radially centered on a predetermined axis, the method comprising the steps of:
    applying cone beam energy from a cone beam source to at least a portion of the object;
    defining a source scanning trajectory as a path traversed by the source;
    using the cone beam source fixed relative to an area detector with both source and detector movably positioned relative to the object to scan about the object;
    specifying the source scanning trajectory as a helical path defining a plurality of mutually spaced stages on a predetermined geometric surface surrounding the field of view such that each plane passing through the field of view intersects the scanning trajectory in at least one point, the area detector having a predetermined dimension extending sufficiently along a direction generally parallel to the predetermined axis to span at least the two consecutive stages having the largest spacing therebetween, thereby obviating the predetermined dimension of the detector from fully spanning the field of view along the predetermined axis;
    scanning at a plurality of positions along the source scanning trajectory to obtain cone beam projection data corresponding to respective portions of the object; and
    using the cone beam projection data to provide a data set which can be reconstructed into an image of the object.

2. A method in accordance with claim 1 wherein the field of view is cylindrical.

3. A method in accordance with claim 2 wherein the geometric surface surrounding the field of view is cylindrical.

4. A method in accordance with claim 3 wherein the spacing between any two successive stages along the predetermined axis is substantially equidistant.

5. A method in accordance with claim 1 which comprises moving the source along the scanning trajectory in a step-wise scan.

6. A method in accordance with claim 1 which comprises moving the source along the scanning trajectory in a continuous scan.

7. A method in accordance with claim 1 wherein the step of using the cone beam source comprises maintaining the source and detector in stationary positions while translating and rotating the object so as to effect relative movement of the source with respect to the object.

8. A method in accordance with claim 1 wherein the step of using the cone beam source comprises maintaining the object in a stationary position while moving the source and detector to achieve relative movement of the source with respect to the object.

9. A method in accordance with claim 1 wherein the predetermined dimension is the height dimension of the detector.

10. A method in accordance with claim 1 wherein the predetermined dimension is the width dimension of the detector.

11. A scanning and data acquisition method for three dimensional computerized tomography (CT) imaging of an object in a field of view radially centered on a predetermined axis, the method comprising the steps of:
applying cone beam energy from a cone beam source to at least a portion of the object;
defining a source scanning trajectory as a path traversed by the source;
using the cone beam source fixed relative to an area detector with both source and detector movably positioned relative to the object to scan about the object;
specifying the source scanning trajectory as a helical path defining a plurality of mutually spaced stages on a predetermined geometric surface surrounding the field of view such that each plane passing through the field of view intersects the scanning trajectory in at least one point, the area detector having a predetermined dimension extending sufficiently along a direction generally parallel to the predetermined axis to span at least the two consecutive stages having the largest spacing therebetween, thereby obviating the predetermined dimension of the detector from fully spanning the field of view along the predetermined axis;
scanning at a plurality of positions along the source scanning trajectory to obtain cone beam projection data corresponding to respective portions of the object;
using the cone beam projection data to provide a data set which can be reconstructed into an image of the object; and
displaying the image of the object based upon the reconstructed data set.

12. A method in accordance with claim 11 wherein the field of view is cylindrical.

13. A method in accordance with claim 12 wherein the geometric surface surrounding the field of view is cylindrical.

14. A method in accordance with claim 13 wherein the spacing between any two successive stages along the predetermined axis is substantially equidistant.

15. A method in accordance with claim 11 which comprises moving the source along the scanning trajectory in a step-wise scan.

16. A method in accordance with claim 11 which comprises moving the source along the scanning trajectory in a continuous scan.

17. A method in accordance with claim 11 wherein the step of using the cone beam source comprises maintaining the source and detector in stationary positions while translating and rotating the object so as to effect relative movement of the source with respect to the object.

18. A method in accordance with claim 11 wherein the step of using the cone beam source comprises maintaining the object in a stationary position while moving the source and detector to achieve relative movement of the source with respect to the object.

19. A method in accordance with claim 11 wherein the predetermined dimension is the height dimension of the detector.

20. A method in accordance with claim 11 wherein the predetermined dimension is the width dimension of the detector.

21. A scanning and data acquisition system for three-dimensional computerized tomography (CT) imaging of an object in a field of view radially centered on a predetermined axis, the system comprising:
a cone beam source for applying cone beam energy to at least a portion of the object;
a two-dimensional area detector positioned to receive cone beam energy from the source;
a scanning device causing relative motion of the source and the object such that the source moves along a scanning trajectory relative to the object;
trajectory defining means operatively coupled to the scanning device to cause the scanning device to provide a helical path having a plurality of mutually spaced stages on a predetermined geometric surface surrounding the field of view such that each plane passing through the field of view intersects the scanning trajectory in at least one point, the area detector having a predetermined dimension extending sufficiently along a direction generally parallel to the predetermined axis to span at least the two consecutive stages having the largest spacing therebetween, thereby obviating the predetermined dimension of the detector from fully spanning the field of view along the predetermined axis;
means for acquiring cone beam projection data with the source at a plurality of positions along the source scanning trajectory, the cone beam projection data corresponding to respective portions of the object; and
means for using the acquired cone beam projection data to generate a data set which can be reconstructed into an image of the object.

22. The system in accordance with claim 21 further comprising a display connected to the using means for displaying an image of the object based upon the generated data set.

23. The system in accordance with claim 22 wherein the geometric surface surrounding the field of view is cylindrical.

24. The system in accordance with claim 23 wherein the spacing between any two successive stages along the predetermined axis is substantially equidistant.

25. The system in accordance with claim 21 wherein the scanning device is adapted to move the source along the scanning trajectory in a step-wise scan.

26. The system in accordance with claim 21 wherein the scanning device is adapted to move the source along the scanning trajectory in a continuous scan.

27. The system in accordance with claim 21 wherein the scanning device comprises a two-axis CNC part manipulator connected to the object for translating and rotating the object so as to effect relative movement of the source with respect to the object while the source and detector remain stationary.

28. The system in accordance with claim 21 wherein the scanning device comprises a two-axis CNC part manipulator connected to the source and detector to achieve relative movement of the source with respect to the object while the object remains stationary.

29. The system in accordance with claim 21 wherein the predetermined dimension is the height dimension of the detector.

30. The system in accordance with claim 21 wherein the predetermined dimension is the width dimension of the detector.

* * * * *